United States Patent
Seibold et al.

(10) Patent No.: US 8,945,098 B2
(45) Date of Patent: Feb. 3, 2015

(54) SURGICAL MANIPULATION INSTRUMENT

(75) Inventors: Ulrich Seibold, Burnaby (CA); Sophie Thielmann, Munich (DE)

(73) Assignee: Deutsches Zentrum fuer Luft-Und Raumfahrt E.V., Cologne (DE)

( * ) Notice: Subject to any disclaimer, the term of this patent is extended or adjusted under 35 U.S.C. 154(b) by 46 days.

(21) Appl. No.: 13/514,235

(22) PCT Filed: Nov. 30, 2010

(86) PCT No.: PCT/EP2010/068506
§ 371 (c)(1), (2), (4) Date: Sep. 5, 2012

(87) PCT Pub. No.: WO2011/069863
PCT Pub. Date: Jun. 16, 2011

(65) Prior Publication Data
US 2012/0330286 A1    Dec. 27, 2012

(30) Foreign Application Priority Data

Dec. 7, 2009    (DE) .................. 10 2009 060 987

(51) Int. Cl.
*A61B 19/00*    (2006.01)
*A61B 17/29*    (2006.01)
*A61B 17/00*    (2006.01)

(52) U.S. Cl.
CPC ............. *A61B 17/2909* (2013.01); *A61B 17/29* (2013.01); *A61B 2017/00464* (2013.01); *A61B 2017/2922* (2013.01); *A61B 2019/4868* (2013.01)
USPC .......................................................... 606/1

(58) Field of Classification Search
CPC ............. A61B 17/2909; A61B 17/295; A61B 2019/4868; A61B 2017/00353; A61B 2017/0046; A61B 2017/292; A61B 2017/2938
See application file for complete search history.

(56) References Cited

U.S. PATENT DOCUMENTS 5,676,678 A * 10/1997 Schad ........................... 606/170
6,491,707 B2   12/2002 Makower et al.
(Continued)

FOREIGN PATENT DOCUMENTS

WO    03077769    9/2003

OTHER PUBLICATIONS

International Search Report dated Apr. 19, 2011 for PCT application No. PCT/EP2010/068506.
English Translation of the Written Opinion of the International Search Authority in corresponding International Application No. PCT/EP2010/068506 dated Jun. 12, 2012.
(Continued)

*Primary Examiner* — Gary Jackson
*Assistant Examiner* — Boniface N Nganga
(74) *Attorney, Agent, or Firm* — Ohlandt, Greeley, Ruggiero & Perle, LLP (57) ABSTRACT

A surgical manipulation instrument which is particularly suitable for minimal invasive surgery, comprising an extra-corporeal drive device and a partial intra-corporeal manipulator part. The drive device comprises several axially displaceable first actuation elements. The first actuation elements are detachably connected to axially displaceable second actuation elements, by a coupling device, the second actuation elements being used to actuate an end effector. The coupling device comprises two coupling elements, one of the coupling elements having undercut recesses in which the second coupling element engages.

12 Claims, 6 Drawing Sheets

(56) References Cited

U.S. PATENT DOCUMENTS

| | | | |
|---|---|---|---|
| 6,673,092 B1* | 1/2004 | Bacher | 606/205 |
| 2001/0031983 A1 | 10/2001 | Brock et al. | |
| 2003/0055409 A1 | 3/2003 | Brock | |
| 2008/0021278 A1* | 1/2008 | Leonard et al. | 600/129 |

OTHER PUBLICATIONS

English Translation of International Preliminary Report on Patentability in corresponding International Application No. PCT/EP2010/068506 dated Jun. 12, 2012.

* cited by examiner

SURGICAL MANIPULATION INSTRUMENT

BACKGROUND

1. Field of the Disclosure

The disclosure refers to a surgical manipulation instrument comprising a coupling detachably connecting an extra-corporeal drive portion and a partially intra-corporeal manipulator part.

2. Discussion of the Background Art

Surgical instruments that are not designed for single use, but for multiple use, have to be sterilized after each single use. Sterilizing can be performed using non-thermal or thermal methods. In everyday clinical practice, sterilizing is generally performed using thermal methods, in particular the so-called autoclaving. In autoclaving, the instrument to be sterilized is exposed for a certain time to water vapor under very high pressure which must wet all surfaces to be sterilized. In the autoclave, the instrument to be sterilized is exposed to temperatures up to 156° C. and pressures up to 2 bar for a period of up to 40 min. Autoclaving must be repeated after each use of the instrument so that in the course of an instrument's lifetime up to several hundreds of autoclaving processes may be passed.

Ever since the 1980ies, the importance of so-called minimally invasive surgery has increased. Here, long, slender manipulation instruments are advanced through only small openings in the epidermis. The intra-corporeal operative field is observed using a rod-shaped camera, introduced in the same manner, and an extra-corporeal monitor. Minimally invasive surgery offers advantages in particular for the patient, namely little traumatizing, short convalescence times, less post-operative pain, lower blood loss, lower risk of infection, lower risk of wound healing disturbances, better cosmetic results, etc. The disadvantages of minimally invasive surgery include, among others, the limited freedom of movement of the surgical instruments. Since the passage opening in the epidermis and the fat tissue can be seen as being a stationary opening forming an invariable point, this results in inverted movement ratios or an impeded hand-eye coordination with respect to the monitor image. Two degrees of freedom of movement are bound by the invariable point, i.e. not every point in the working area can be reached under any optional orientation of the functional instrument end.

Minimally invasive manipulation instruments that offer additional intra-corporeal degrees of freedom of movement may provide enhanced intra-corporeal manipulability and thus represent a considerable improvement in minimally invasive surgery. The additional degrees of freedom have to be moved precisely. This may possibly be achieved by manual operation, however, this requires great aptness and long practice. Therefore, a robot-assisted remote manipulation approach is advisable, where the surgeon sits at an ergonomically shaped console, remote from the patient, and guides the surgical manipulation instrument via an appropriate man-machine interface without having to think about the cinematic and its activation. Here, the surgical manipulation instrument is actuated in a computer-assisted manner and performs the movement corresponding to the surgeon's intentions.

However, the actuators for driving the surgical manipulation instrument can generally not be autoclaved. Therefore, it is required that the extra-corporeal drive portion is separable from the partially intra-corporeal manipulator part.

The surgical manipulation instrument is thus bipartite and, by means of a coupling, is adapted to be separated into an extra-corporeal drive portion and an intra-corporeal manipulator part.

A surgical manipulation instrument is known from U.S. Pat. No. 6,491,707 A1, which comprises a coupling for separating the drive portion from the manipulator part. Here, the drive device rotates actuation elements such as shafts and transmits the rotational and torsional movements to actuation elements of the manipulator part via the coupling device. The end effector of the manipulator part is actuated through the second actuation elements. The coupling parts each have rotatable coupling bodies comprising axial pins and bores, respectively, and are coupled or uncoupled in the axial direction. Since the rotatable opposite coupling bodies cannot be coupled together if they are not in precise alignment, a search run must be performed for all coupling body pairs upon coupling. The coupling bodies each rotate until a position is found in which all coupling body pairs are in a coupling position that allows engagement. A similar coupling is known from US 2001 003 1983 A1. Here, the coupling parts comprise semi-cylindrically shaped coupling bodies. In the interest of a smooth coupling operation it is necessary to provide a certain minimum play between the coupling bodies in the engaged condition. However, this play has adverse effects in the operation of the manipulation instrument or may even make an automatic control impossible.

It is an object of the disclosure to provide a surgical manipulation instrument comprising axially displaceable elements both on the drive side and on the manipulator side, wherein the actuation elements are connected by means of a reliable and simple coupling device.

SUMMARY

Newly developed drive means generating axial movements allow an axial displacement, i.e. a displacement in the longitudinal direction, of first actuation elements, such as cables or rods, connected with the drive means, instead of rotating the same. It is also desirable to provide axially displaceable second actuation elements also on the part of the manipulator part in order to actuate the end effector. A linear actuation of the end effector is advantageous with a view to manipulability. When using known coupling devices, it would be necessary to translate the linear movement of the first actuation elements actuated by the drive means into a rotary movement, since known coupling device transmit rotary movements. On the side of the coupling device connected with the manipulator part the rotary movement would then have to be translated into an axial movement again. Such a coupling device in connection with translation means for translating a linear movement into a rotary movement or a rotary movement into a linear movement is extremely intricate. A corresponding coupling device would not only be expensive and elaborate, but would also be heavily fraught with losses. This is inacceptable in particular with surgical instruments used in minimally invasive surgery, since the transmission of forces and moments must be performed with utmost precision and as little play as possible.

The surgical manipulation instrument of the present disclosure, which is particularly suited for minimally invasive surgery, comprises an extra-corporeal drive portion as well as a manipulator part adapted for partial intra-corporeal arrangement. The drive means has a plurality of axially displaceable first actuation elements. The actuation elements may be rods or cables, for instance, via which axial forces are transmitted. The manipulator part also comprises a plurality of axially displaceable, second actuation elements which are also rods and/or cables, for instance. The actuation elements serve to actuate an end effector.

The first actuation elements are connected with the second actuation elements via a coupling device. The coupling device provides for a detachable connection of actuation element pairs. In order to realize a detachable connection the coupling device comprises, according to the disclosure, a first coupling element with an undercut recess into which engages a second coupling element. Thus, by assembling the two coupling elements, the second coupling element engages the undercut recess in the manner of a locking connection. This is preferably achieved by pushing the two coupling elements axially towards each other. The undercut recess has an undercut, seen in the axial direction. Thus, the actuation element pairs can be connected simply by pushing the coupling elements together. This has the advantage that the drive means and the manipulator part can be connected in a simple manner by clinic staff. In particular no special knowledge is required.

In a preferred embodiment the second coupling element has a plurality of pivotable coupling arms. Pivoting is preferably effected by an elastic deformation of the coupling arms upon closing the coupling device. Preferably, the free ends of the coupling arms are provided, in particular, with at least partly radially arranged projections. These projections engage the undercut recess in the closed state of the coupling device. The two coupling elements are thus closed such that the two coupling elements are moved towards each other in the axial direction, with the first coupling element pressing or pivoting the coupling arms of the second coupling element outward, for instance. Pushing the coupling elements further together, the coupling arms are pivoted until they snap back into their initial position and the projections of the coupling arms engage the undercut recess.

Preferably, the first coupling element is of rotationally symmetric design, where it is particularly preferred that the undercut recess is annular. In a preferred embodiment, the coupling arms are correspondingly arranged on a circular ring, with the coupling arms embracing the first coupling element when the coupling device is in the closed state. The preferred design of the first coupling element as a rotationally symmetric coupling element offers the particular advantage that the parts to be coupled can be connected in a simple manner, since no orientation of the parts with respect to each other is required.

Furthermore, it is preferred that the first coupling element is rigid and thus has a great strength. In particular it is a solid body. This allows for a small structural size.

In order to guarantee as safe a connection of the two coupling elements as possible, it is preferred that the first coupling element comprises a plurality of undercut recesses that are arranged, in particular, one after the other in the axial direction. The recesses, which in a particular embodiment are each annular in shape, are preferably designed such that their diameter increases step-wise. The coupling arms correspondingly comprise a plurality of projections engaging the different undercut recesses in the closed state of the coupling device.

The first and/or the second coupling element are preferably firmly connected with the corresponding fastening element or may also be formed integrally with the same. Thereby, space requirements are reduced.

Preferably, the coupling elements of the coupling device are fixed or held exclusively by a clamping from outside. Thereby, the structural space can be reduced further.

In a particularly preferred embodiment, a fixing element is provided in addition. The fixing element serves to retain the coupling elements in the closed position. The fixing element thus helps to avoid an unintentional opening of the coupling device. If the second coupling element has coupling arms that are pivoted outward to be opened or closed, a fixing element may be provided that surrounds the coupling arms in the closed position and thereby prevents an outward directed pivoting of the coupling arms. Preferably, a slidable sleeve is provided as the fixing element. When the coupling device is closed, the sleeve surrounds the two coupling elements at least partly. It is advantageous, in particular when coupling arms are provided, to provide an annular sleeve that surrounds the coupling arms at least in the region of the radially extending projections. Opening the coupling device then merely requires shifting the sleeve so that the two coupling elements can be pulled apart again, where, if the second coupling element has coupling arms, these can be pivoted again. Preferably, the fixing element is spring-loaded, with the spring load being such that the fixing element has to be shifted against the spring force from the closed position to the open position. This guarantees that the operating staff cannot forget to arrange the fixing element in the closed position.

In a further preferred embodiment of the disclosure the second coupling element comprises radially displaceable holding elements such as balls or the like. By shifting the holding elements radially into the undercut recess, the coupling device is closed. A fixing element, which is preferably provided, helps to avoid that the holding elements move out from the undercut recess by themselves. This may be effected, for example, by making the individual holding elements spring-loaded on the direction of undercut recess. It is also possible to configure the fixing element such that it comprises a recess into which the balls can be shifted in order to release the coupling device, and to arrange the fixing element such that, in order to close the coupling device, the recess is offset towards the holding elements. In this case, the fixing element may again be designed to be displaceable.

In a preferred development of the disclosure, the first coupling element comprises an axial bore into which the second coupling element or a pin-shaped projection of the second coupling element can be inserted. In this embodiment the undercut recess is provided on an inner side of the bore. Again, projections of coupling arms or holding elements may engage the undercut recesses.

In a preferred embodiment the fixing element is arranged for radial displacement in the second coupling element. Here, the fixing element, which is substantially pin-shaped in this embodiment, comprises at least one recess into which the holding elements, embodied in the form of balls, can slide in order to open the coupling element. When the fixing element is shifted into the closed position, the fixing element presses the balls into the undercut recesses in the inner side of the axial bore of the first coupling element.

According to a further preferred embodiment of a surgical manipulation instrument, which represents an independent disclosure, the undercut recess may also be open to the side. The opening of the undercut recess thus forms an angle different from 0°, in particular of 90°, with the longitudinal axis of the corresponding actuation element. In this development, the second coupling element comprises a projection that is inserted into the undercut recess from the side. Here, it is particularly preferred that all first coupling elements have an undercut recess, whose openings are respectively oriented in the same direction. Thus, it is possible to introduce the projections of the second coupling elements into the undercut recess together. In particular, the second coupling elements comprise projections with a cylindrical cross section, where the undercut recesses are shaped similar to a slot and have a curvature at their ends that substantially corresponds to the radius of the cylinder-shaped projection. Of course other geometric forms are conceivable, where it is preferred that the outer shape of the second coupling elements or of the projections of the second coupling elements is complementary with the shape of the undercut recess.

In another embodiment the undercut recesses are also open to the side and in particular form an opening angle of 90° with the longitudinal direction of the actuation elements. The opening direction of the individual undercut recesses is preferably located on a circular line. In a preferred embodiment, the second coupling elements again comprise projections. Here, the projections, which are in particular cylindrical in shape, are inserted into the undercut recesses by pivoting the projections.

The following is a detailed description of the disclosure with reference to preferred embodiments and to the accompanying drawings.

DETAILED DESCRIPTION OF THE PREFERRED EMBODIMENT

A surgical manipulation instrument according to the present disclosure, which is especially suited for use in minimally invasive surgery, comprises an extra-corporeal drive device 10. The same may, in particular, comprise one or a plurality of electric motors and transmissions whereby actuation elements 12 (FIG. 2) are displaced in the axial direction (arrows 14).

Figure 2:
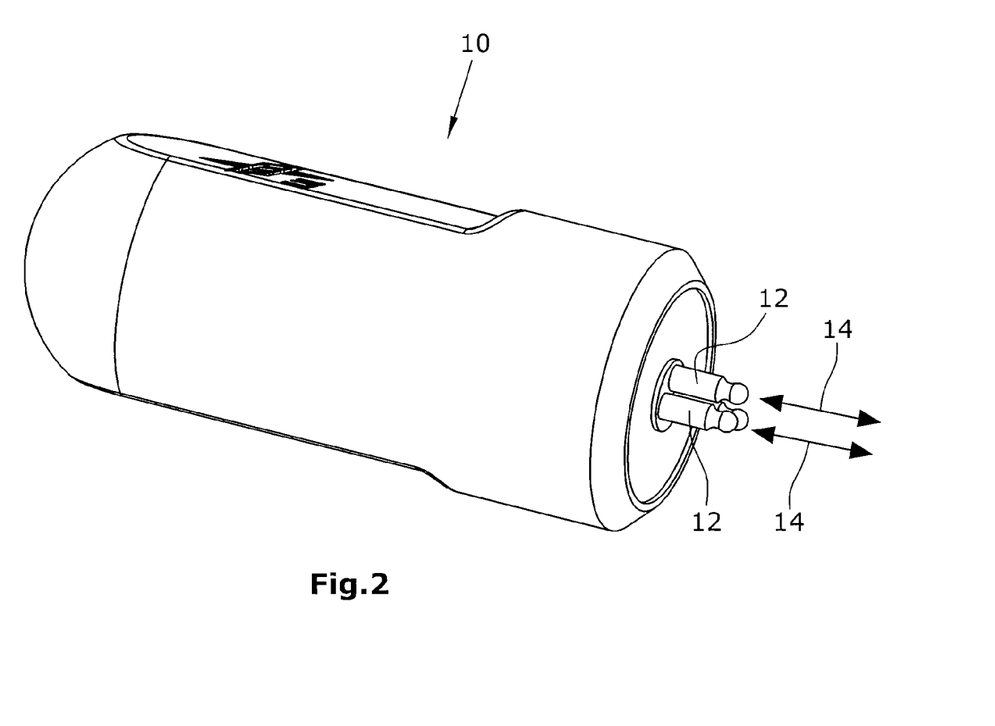
FIG. 2 is a schematic perspective side elevational view of the drive device.

In the embodiment illustrated, the first actuation elements 12 are in the form of rods. However, they may also be cables via which only pulling forces are transmitted.

Figure 1:
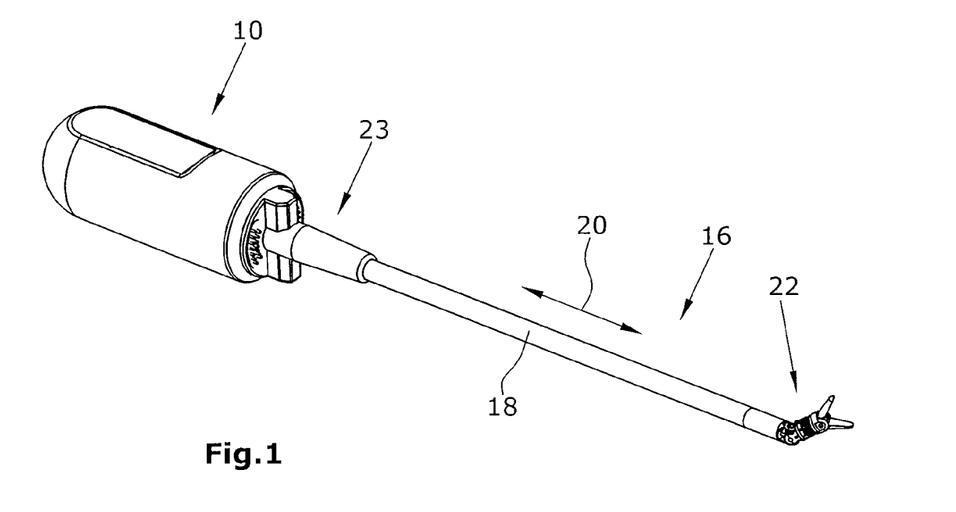
FIG. 1 is a schematic perspective view of a surgical manipulation instrument.

Further, the surgical manipulation instrument comprises a manipulator part 16 (FIG. 1). Within a tubular shaft 18, rod-shaped second actuation elements are arranged. These are adapted to be displaced in the longitudinal direction 20. The second actuation elements are connected with an end effector 22. Displacing the second actuation elements thus causes a manipulation of the end effector. Again, the second actuation elements may be rod-shaped actuation elements, but also actuation cables.

A coupling device 23 is provided for the connection of the first actuation elements 12 and the second actuation elements arranged in the tubular shaft.

Figure 3:
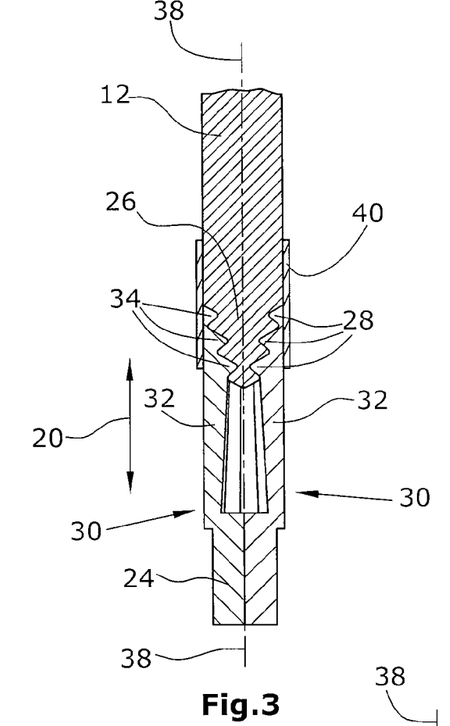
FIG. 3 is a schematic sectional view of a part of a first preferred embodiment of a coupling device.
Figure 4:
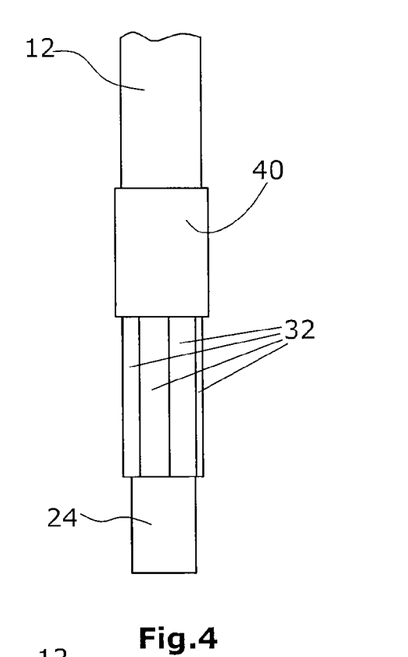
FIG. 4 is a schematic top plan view on the portion of the coupling device illustrated in FIG. 2.
Figure 5:
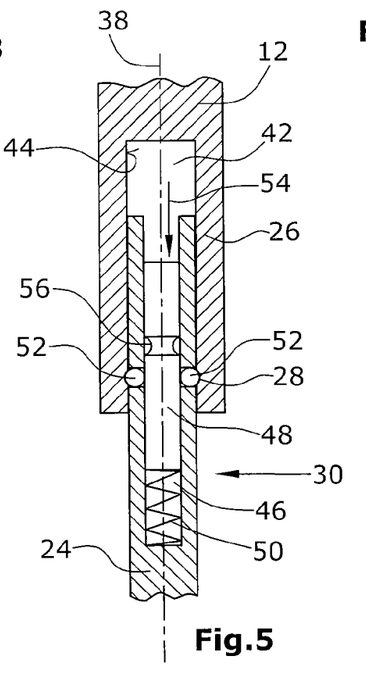
FIG. 5 is a schematic sectional view of another embodiment of a portion of a coupling device.

The illustrations in FIGS. 3-5 respectively show parts of the coupling device of respective embodiments. For the sake of simplicity, a first and a second actuation element is shown, respectively. Typically, both the drive device 10 and the manipulator part 16 comprise at least two, in particular at least three such actuation elements. These are preferably coupled or uncoupled simultaneously.

In the first embodiment of the disclosure, illustrated in FIGS. 3 and 4, a first actuation element 12 and a second actuation element 24 are shown. At its end, the actuation element 12 has a frustoconical projection forming a first coupling element 26. In the embodiment illustrated, the same comprises three undercut recesses 28, each annular in shape. The recess 28 illustrated forms an undercut in the axial or the longitudinal direction, respectively, of the actuation elements 12 and 24.

At the end directed towards the first actuation element 12, the second actuation element 24 has a second coupling device 30. In the embodiment illustrated, the coupling element 30 comprises a plurality of coupling arms 32. The coupling arms 32 have their free end provided with radial projections 34, directed inward in the embodiment illustrated. With the coupling device closed, as illustrated in FIG. 3, the projections 34 engage in the undercut recesses 28. This is possible because the coupling arms are resilient and are essentially resiliently pivotable about a point 36. As a result, when the two coupling elements 26, 30 are pushed together, the coupling arms 32 are pressed outward until the two coupling elements are in the closed position and the projections 34 lock into the undercut recess 28.

In the embodiment illustrated, a plurality of annular undercut recesses 28 is provided. Their respective diameter increases, seen from the bottom to the top in FIG. 3, and as such they are arranged in steps. The first coupling element 26, as well as the first actuation element 12, which in the embodiment illustrated is formed integrally with the coupling element, are rotationally symmetric with respect to a longitudinal axis 38.

In the embodiment illustrated, the second coupling element 30 comprises a plurality of coupling arms 32 arranged on a circular line. In the embodiment illustrated, these are also formed integrally with the second actuation element 24. The actuation element 24 is also rotationally symmetric with respect to the longitudinal axis 38.

In order to guarantee that the coupling arms 32 will remain in the closed position, a fixing element 40 is provided. In the embodiment illustrated, the fixing element is a sleeve displaceable in the longitudinal direction 20. In the closed state of the coupling device, the sleeve 40 surrounds the two coupling elements 26, 30. Since the coupling arms 32 have to be pivoted outward to open the coupling, the sleeve 40 helps to avoid an unintentional opening of the coupling device. In order to open the coupling device, the sleeve 40 would have to be shifted upward in FIG. 3. In this position, the two coupling elements 26, 30 can then be pulled apart axially. Since, typically, two or more actuation element pairs 12-24 are connected with each other, in particular at the same time, it is preferred that the sleeves 40 are displaceable relative to each other in use, while they are stationary with respect to the actuation elements 12-24.

It is also possible that the first coupling element is spherical in shape, for instance, and that it is fixedly connected with the first actuation element 12. An undercut recess is formed in such a sphere as well, for corresponding radial projections of coupling arms to engage.

In the further embodiment of the disclosure illustrated in FIG. 5, identical components are identified by the same reference numerals.

In this embodiment the first coupling element 26 is again rotationally symmetric with respect to the longitudinal axis 38. The substantially cylindrical first coupling element 26 comprises a centered, central bore 42 extending in the axial direction. The undercut recess 28, again annular in shape, is formed on an inner side 44 of the bore 42.

The second coupling element 30 is rod-shaped in the embodiment illustrated and, as illustrated in FIG. 5, inserted in the axial bore 42 to close the coupling device. The second coupling element 30 also has a central bore 46 extending in the axial direction. Arranged therein is a fixing element 48, which is rod-shaped in the embodiment illustrated, the rod-shaped fixing element 48 being constantly urged towards the first actuation element 12 by a spring 50. In this position, holding elements 52, which are balls in the embodiment illustrated, abut on the smooth, cylindrical outer surface of the fixing element 48. As a result, the balls 52 are pressed radially outward into the undercut recess 28 in FIG. 5. Consequently, the coupling element is in a closed position. Due to the spring load on the fixing element 48, an automatic unintentional opening is prevented. In order to open the coupling device, it is necessary to displace the fixing element 48 in the direction of the arrow 54, i.e. in the direction of the second actuation element 24. This may be effected, e.g., by means of a non-illustrated pin shaped projection passing outward through a slot-shaped opening in the coupling element 30. Displacing this projection causes the displacement of the fixing element 48. Since this embodiment again provides at least two actuation element pairs 12-24, it is again preferred that the fixing elements 48 are actuatable in common.

The displacement of the fixing element 48 in the direction of the arrow 54 causes the displacement of the recess 56 to the level of the balls 52. Thereby, it is possible to pull the second actuation element 24 from the axial bore 42, since the balls 52 are adapted to be displaced radially inward.

Of course, it is also possible to combine the two above described embodiments, in particular, to couple individual actuation element pairs described with reference to FIGS. 3, 4 and others described with reference to FIG. 5.

A further embodiment (FIGS. 6 and 7) represents an independent disclosure with respect to the coupling device. This coupling device also serves to connect first actuation means 12, which in the embodiment illustrated are rods, with second actuation means 24 which are also rod-shaped actuation means. As explained with reference to the above embodiments, the actuation means 12, 24 are connected with a drive device 10 (FIG. 1) and an end effector 22.

Figure 6:
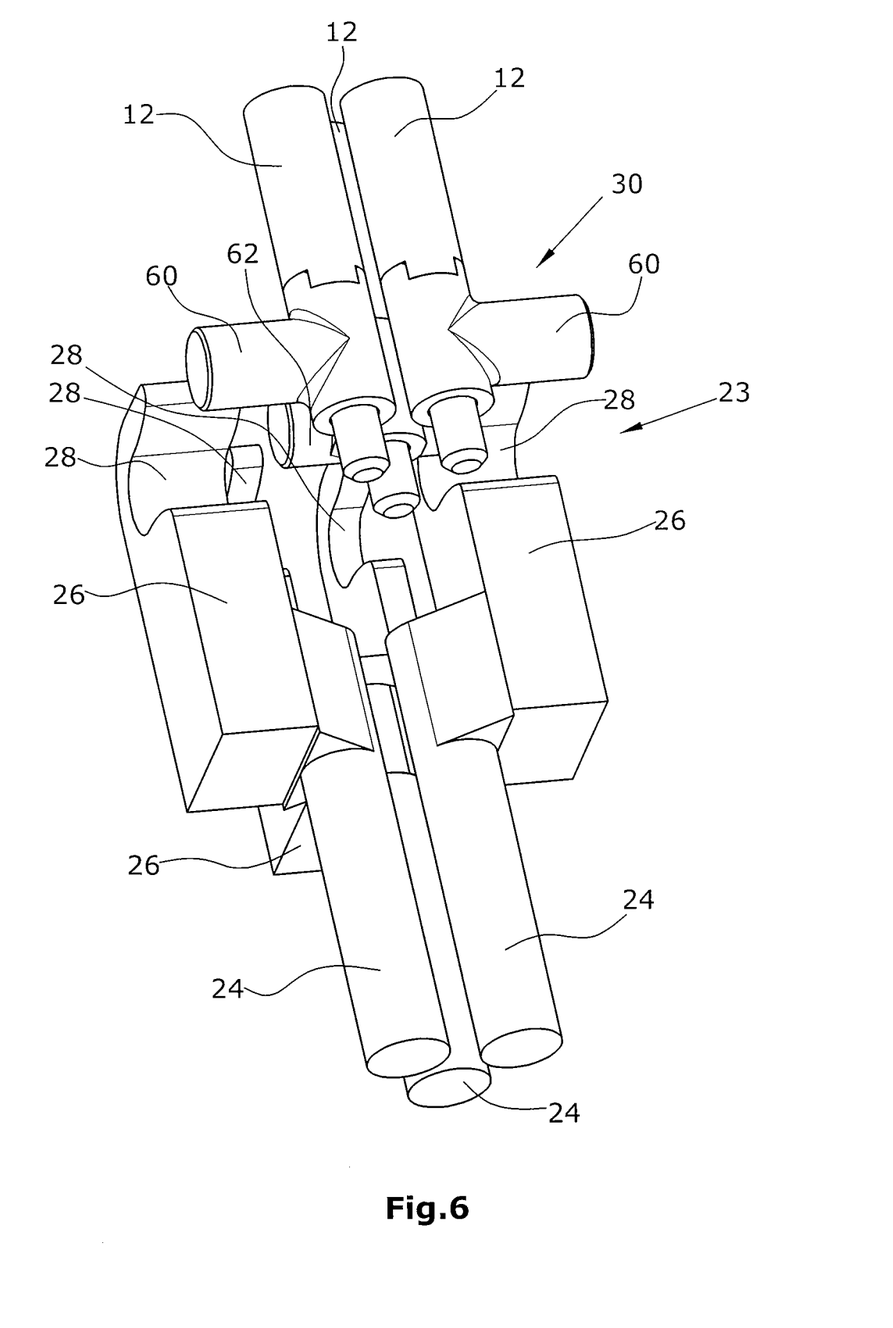
FIG. 6 is a schematic perspective view of a further embodiment of a coupling device in the uncoupled state.
Figure 7:
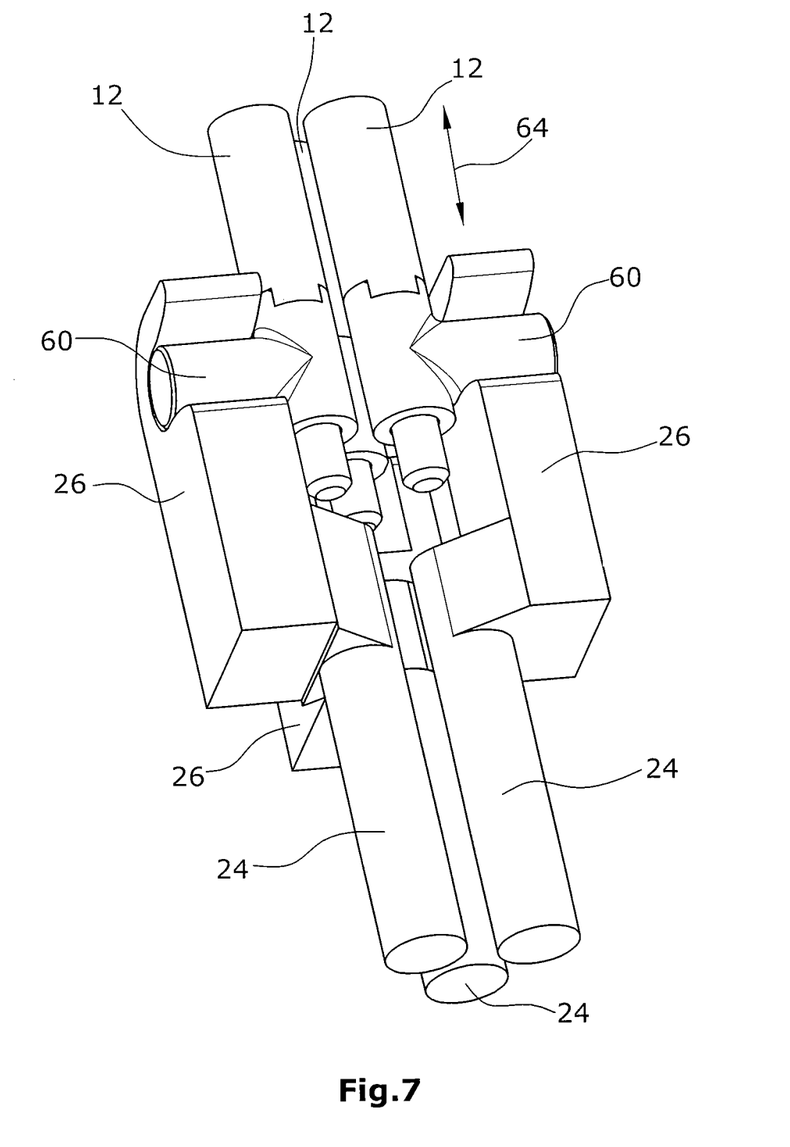
FIG. 7 is a schematic perspective view of the coupling device illustrated in FIG. 6, the coupling device being in the coupled state.

In order to form the coupling device 23, the second actuation means 24 are connected with first coupling elements 26. These respectively comprise an undercut recess 28. In the embodiment illustrated, all undercut recesses 28 face in the same direction. Further, the undercut recesses 28 form an angle of 90° with respect to the longitudinal axes of the second actuation means 24 so that the undercut recesses 28 are open to the side.

In the embodiment illustrated, the first coupling elements 30 connected with the first actuation means 12, comprise a cylindrical pin 60. The two front pins 60 in FIG. 6 face in opposite directions. In order to allow the pins 60 to be inserted into the undercut recesses 28 together, the pin 62 of the rear actuation element 12 extends in both directions and engages in both parts 28 of the rear undercut recess. Upon insertion into the divided undercut recess 28, the pin 62 is passed between the two first coupling elements 26.

In the inserted state (FIG. 7), axial forces can be transmitted by the first actuation means 12 to the second actuation means 24 in the direction of an arrow 64, i.e. in the direction of the longitudinal axes of the first actuation means 12.

Figure 8:
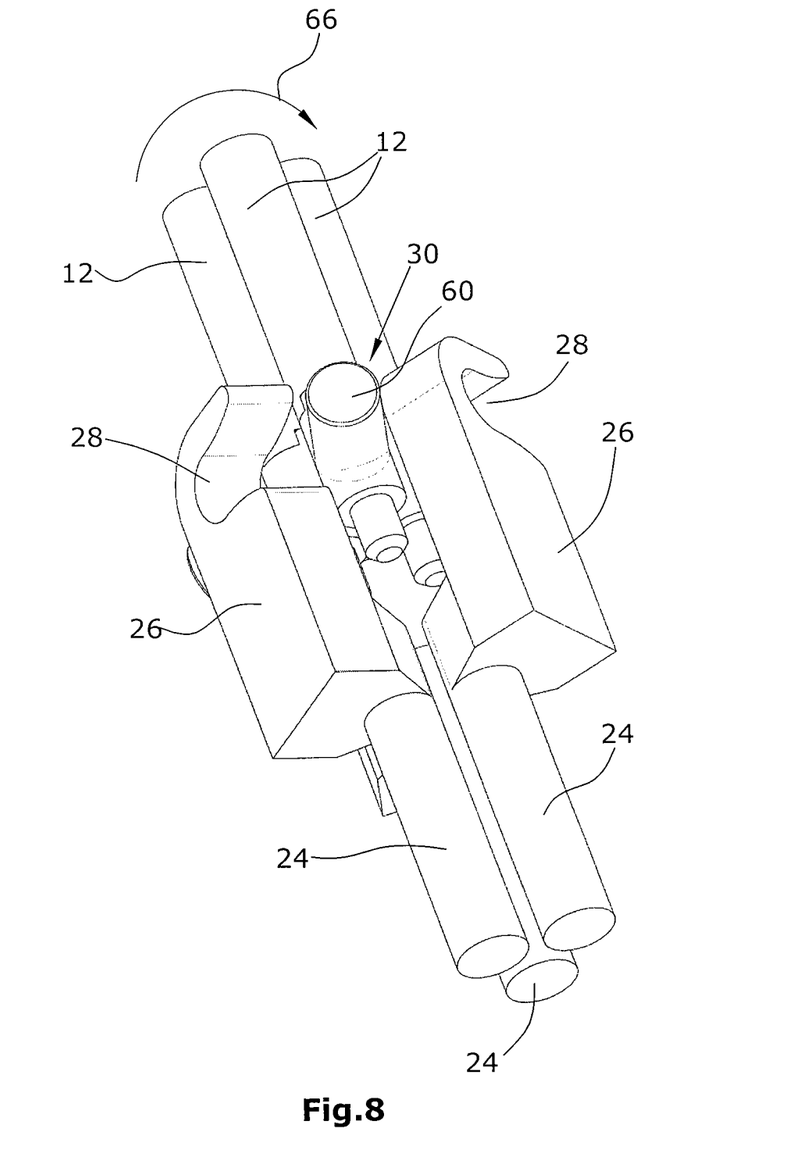
FIG. 8 is a schematic perspective view of a further embodiment of a coupling device in the uncoupled state.
Figure 9:
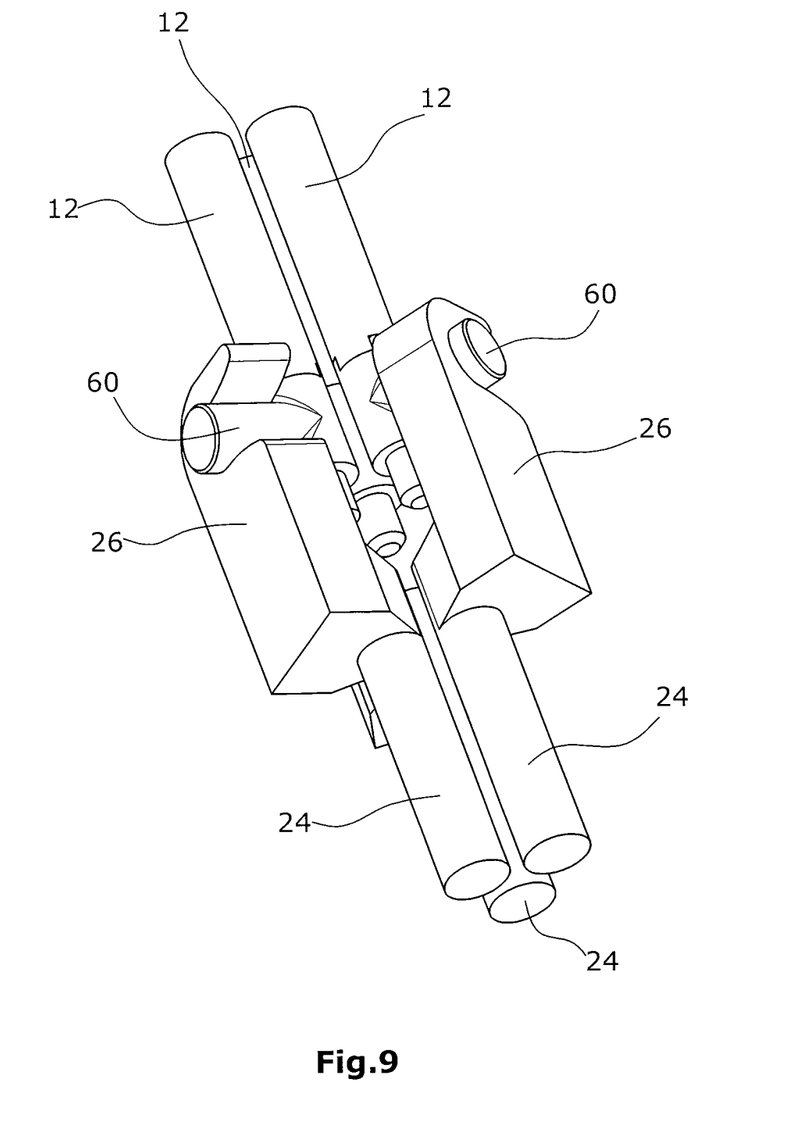
FIG. 9 is a schematic perspective view of the coupling device illustrated in FIG. 8, the coupling device being in the coupled state.

Still another embodiment of a further coupling device 32 which also represents an independent disclosure (FIGS. 8 and 9) is provided, which is an embodiment similar to the embodiment illustrated in FIGS. 6 and 7. The essential difference is that coupling is effected by commonly turning the first actuation elements 12 in the direction of an arrow 66 (FIG. 8). Accordingly, the undercut recesses 28 of the first coupling elements 26 are arranged on a circular line and are open in a tangential direction. In this embodiment featuring three first actuation means 12, the same respectively have cylindrical projections 60 extending radially outward. The latter form an angle of 90° with the longitudinal axis of the respective first actuation means. Among them, the pins include an angle of 120°. The three actuation elements 12, including the first coupling elements 30, are identical in this embodiment. This is also true for the second actuation elements 24 in connection with the first coupling elements 26.

What is claimed is:

1. A surgical manipulation instrument, comprising:
   an extra-corporeal drive device comprising a plurality of axially displaceable first actuation elements,
   a partially intra-corporeal manipulator part comprising a plurality of axially displaceable second actuation elements for actuating an end effector, and
   a coupling device for detachable coupling of said first and second actuation elements pairs, said coupling device comprising a plurality of first coupling elements for each actuation elements pair, each with an undercut recess into which a second coupling element engages,
   wherein each actuation element pair is independently axially displaceable with respect to the other actuation elements pairs when the first and second actuation elements are coupled,
   wherein each of the plurality of the first coupling element is rotationally symmetric with respect to its longitudinal axis that coincides with a longitudinal axis of a corresponding first actuation element and second actuation element, wherein no orientation of said first and second coupling elements is required during coupling thereof.

2. The surgical manipulation instrument of claim 1, wherein the second coupling element comprises pivotable coupling arms having their free ends provided with a radially arranged projection, which engages into the undercut recess when the coupling device is in a closed state.

3. The surgical manipulation instrument of claim 2, wherein the coupling arms are arranged on a circular ring and surround the first coupling element when the coupling device is in the closed state.

4. The surgical manipulation instrument of claim 1, wherein the undercut recess is annular in shape.

5. The surgical manipulation instrument of claim 1, wherein the first coupling element comprises a plurality of undercut recesses arranged one after the other in the axial direction.

6. The surgical manipulation instrument of claim 4, wherein the diameter of the annularly shaped undercut recesses increases step-wise in the axial direction.

7. The surgical manipulation instrument of claim 1, wherein the first and/or the second coupling element is/are rigidly connected with the first or the second actuation element, respectively.

8. The surgical manipulation instrument of claim 1, further comprising a fixing element for holding the coupling elements in a closed position in order to prevent the coupling device from being opened.

9. The surgical manipulation instrument of claim 8, wherein the fixing element at least partly surrounds the coupling elements in the closed position, the fixing element comprising an axially displaceable sleeve.

10. The surgical manipulation instrument of claim 1, wherein the second coupling element comprises holding elements, adapted to be displaced radially into the undercut recess, for closing the coupling device.

11. The surgical manipulation instrument of claim 1, wherein the first coupling element comprises an axial bore into which the second coupling element may be inserted, the undercut recess being provided on an inner side of the bore.

12. The surgical manipulation instrument of claim 10, wherein, in the closed position, an axially displaceable fixing element presses the holding elements radially outward and comprises a recess into which the holding elements slide for opening.

\* \* \* \* \*